United States Patent [19]

Morinaka et al.

[11] 4,086,349
[45] Apr. 25, 1978

[54] QUINOLOPYRAN-4-ONE-2-CARBOXYLIC ACID DERIVATIVES AND SALTS THEREOF AS NOVEL COMPOUNDS AND AS MEDICINES FOR TREATMENT OF ALLERGIC ASTHMA

[75] Inventors: Yasuhiro Morinaka; Kazuo Takahashi, both of Ibaraki, Japan

[73] Assignee: Mitsubishi Yuka Pharmaceutical Co., Ltd., Japan

[21] Appl. No.: 709,779

[22] Filed: Jul. 29, 1976

[30] Foreign Application Priority Data

Jul. 30, 1975 Japan .................................. 50-92939
Mar. 5, 1976 Japan .................................. 51-23792

[51] Int. Cl.$^2$ .................... A61K 31/47; C07D 491/04
[52] U.S. Cl. ............................ 424/258; 260/287 CF
[58] Field of Search ........ 260/287 H, 287 CF, 287 R; 424/258

[56] References Cited

U.S. PATENT DOCUMENTS 3,629,290 12/1971 Cairns et al. ...................... 260/287 R
4,010,270 3/1977 Hess et al. .......................... 424/258

FOREIGN PATENT DOCUMENTS 2,446,497 8/1976 Germany ....................... 260/287 CF Primary Examiner—Donald G. Daus
Assistant Examiner—David E. Wheeler
Attorney, Agent, or Firm—Oblon, Fisher, Spivak, McClelland & Maier

[57] ABSTRACT

Quinolopyran-4-one-2-carboxylic acid derivatives and salts thereof are provided as novel compounds and as medicines for treatment of allergic asthma, each of the derivatives being represented by the general formula

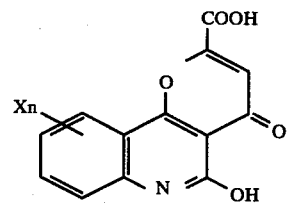

wherein X designates a member selected from the group consisting of alkyl groups having 1 to 5 carbon atoms, alkoxy groups having 1 to 5 carbon atoms, halogen atoms, aryl-substituted alkoxy groups having 7 to 10 total carbon atoms, alkoxycarbonyl groups having 2 to 6 total carbon atoms, and aryl groups having 6 to 10 carbon atoms, and $n$ is any one of the integers 1 through 4, X being the same group or different groups in the case where $n$ is at least 2.

40 Claims, No Drawings

QUINOLOPYRAN-4-ONE-2-CARBOXYLIC ACID DERIVATIVES AND SALTS THEREOF AS NOVEL COMPOUNDS AND AS MEDICINES FOR TREATMENT OF ALLERGIC ASTHMA

SUMMARY OF THE INVENTION

This invention relates to quinolopyran-4-one-2-carboxylic acid derivatives represented by the following general formula I and salts thereof. Furthermore, the invention relates to medicines for treatment of allergic asthma comprising quinolopyran-4-one-2-carboxylic acid derivatives represented by the following general formula I or salts thereof.

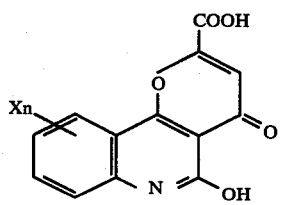

In the above formula: X denotes an alkyl group having 1 to 5 carbon atoms, an alkoxy group having 1 to 5 carbon atoms a halogen atom, an aryl-substituted alkoxy group having 7 to 10 total carbon atoms, an alkoxycarbonyl group having 2 to 6 total carbon atoms, or an aryl group having 6 to 10 carbon atoms; $n$ is an integer of 1 through 4; and X may be the same or may be different in the case where $n$ is 2 or greater.

The nature and further features of this invention will be apparent from the following detailed description beginning with a consideration of general aspects of the invention and concluding with specific examples of compounds in accordance with the invention, an example of a test of these compounds, and examples of production of these compounds.

DETAILED DESCRIPTION

Examples of the groups in formula I set forth above are as follows. Examples of the alkyl group having 1 to 5 carbon atoms are methyl, ethyl, propyl, isopropyl, butyl, and amyl. Examples of the alkoxy group having 1 to 5 carbon atoms are methoxy, ethoxy, n- or isopropoxy, n- iso- or tert- butoxy, and n-, iso, sec- or tert- amyloxy. Examples of the aryl-substituted alkoxy having 7 to 10 total carbon atoms are benzyloxy and phenylethyloxy. Examples of the alkoxycarbonyl group having 2 to 6 total carbon atoms are methoxycarbonyl, ethoxycarbonyl, propyloxycarbonyl, and butoxycarbonyl. Examples of the aryl group having 6 to 10 carbon atoms are phenyl, tolyl, and xylyl. Furthermore, examples of the halogen atom are atoms of chlorine, bromine, iodine, and fluorine.

A compound represented by the above formula I or a salt thereof is produced by causing a quinoline derivative represented by the general formula II set forth below to react with an oxalate represented by the general formula III set forth below in an organic solvent in the presence of a base, subjecting the reaction product to acid treatment thereby to cause it to undergo ring closure, and producing a salt thereof as desired.

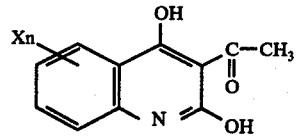

In this general formula II, X and $n$ are the same as in formula I.

In this general formula III, R denotes an alkyl group having 1 to 5 carbon atoms, a phenyl group, or a benzyl group.

The above mentioned reaction can be represented by the following formula.

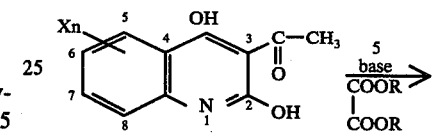

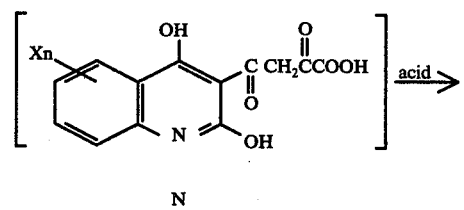

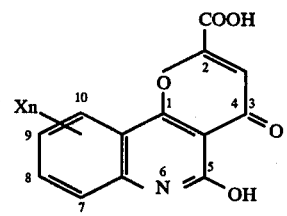

The compound represented by the above formula I may take the form of the following tautomeric structure. Accordingly, this compound is quite logically within the purview of this invention.

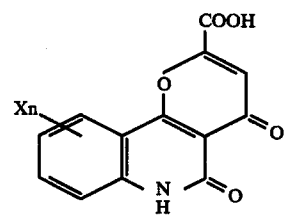

The process of producing the compounds of this invention will now be described in specific terms in relation to the above given reaction formula.

PREPARATION OF INTERMEDIATE OF FORMULA IV

The intermediate of formula IV is prepared by causing a quinoline derivative of formula II to react with an oxalate of formula III in an organic solvent in the presence of a base. The intermediate of formula IV thus obtained is separated and purified by conventional method and thereafter subjected to the succeeding process step. When the above mentioned solvent used is the same as that which can be used in the succeeding process step, however, the base thus used is neutralized, and then the reaction is continued with the system as it is.

Substances Participating in the Reaction

Quinoline Derivative of Formula II

The quinoline derivative of formula II, which is a starting material is prepared by causing an aniline derivative to react with acetyldiethyl malonate in accordance with the process set forth in The Journal of the American Chemical Society, 68, 324 (1946) (reaction formula (i) set forth below) or by a Friedel-Crafts acylation reaction of 2,4-dihydroxyquinoline in accordance with the process set forth in Journal of the Pharmaceutical Society of Japan 71, 1100 (1951) (reaction formula (ii) set forth below).

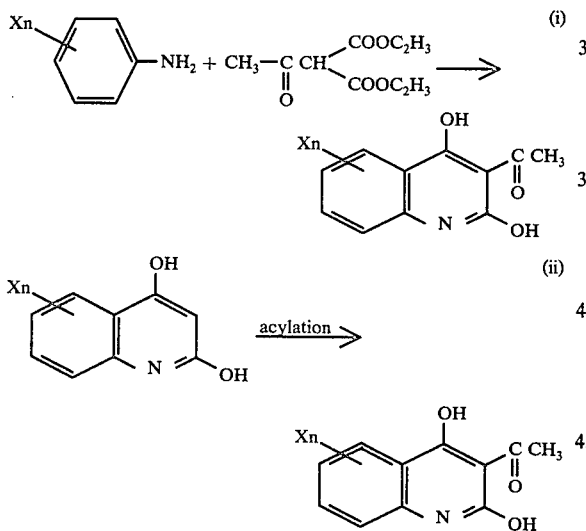

Examples of the quinoline derivative of formula II are the compound of formula II where "$n$" is zero, namely, 2,4-dihydroxy-3-acetyl-quinoline and the compounds of formula II where $n$ is not zero and X is, for example, 7,8-dimethyl-, 6-methyl, 6-ethyl, 6-isopropyl-, 8-methyl-, 6-methoxy-, 7-methoxy-, 8-methoxy-, 6,7-dimethoxy-, 6-isopropoxy-, 6-n-butyl-, 6-chlor-, 6-brom-, 6-fluoro-, 6-benzyloxy-, 6-ethoxycarbonyl-, 6-phenyl-, 8-methyl-6-chlor, 6,8-dimethyl-, or the like.

Oxalate of Formula III

Examples of the oxalate of formula III are dimethyl oxalate, diethyl oxalate, diphenyl oxalate, and dibenzyl oxalate. This oxalate is used in a mole ratio of 0.8 to 20, preferably 1 to 10, with respect to the quinoline derivative of formula II.

Base:

Examples of the base are alcoholates represented by $R_3ONa$ or $R_3OK$, wherein $R_3$ is an alkyl group having 1 to 5 carbon atoms, $NaNH_2$, NaH, NaOH, and KOH. This base is used in a mole ratio of preferably 0.8 to 15, particularly 1 to 10, with respect to the quinoline derivative of formula II.

Reaction Conditions

Temperature, Time

The reaction temperature is of the order of 0° to 200° C, preferably 20° to 170° C, and particularly preferably the reflux temperature.

The reaction time is ordinarily of the order of 0.5 to 5 hours.

Solvent

Examples of the above mentioned solvent are dialkyl ethers such as diethyl ether, dioxane, tetrahydrofuran, ethyl acetate, benzene, toluene, and xylene. This solvent is used in a gravimetric quantity which is 1 to 100 times, particularly 10 to 50 times that of the quinoline derivative of formula II.

PREPARATION OF THE QUINOLOPYRAN-4-ONE-2-CARBOXYLIC ACID DERIVATIVE OF FORMULA I

The compound of formula I is prepared by subjecting the intermediate of formula IV to acid treatment in a solvent thereby to cause the same to undergo ring closure.

Substances Participating in the Reaction

Acid

Examples of the acid are hydrochloric acid, sulfuric acid, acetic acid, para-toluenesulfonic acid, benzene-sulfonic acid, and acidic resins. This acid is used in a mole ratio of 1 to 50, preferably 5 to 10 with respect to the quinoline derivative of formula II or the intermediate of formula IV.

Reaction Conditions

Temperature, Time

The reaction temperature is of the order of 0° to 200° C, preferably 50° to 170° C.

The reaction time is ordinarily 5 minutes to 2 hours.

Solvent

Examples of the solvent are methanol, propanol, xylene, and acetic acid. This solvent is used in a gravimetric quantity of 1 to 200 times, preferably 3 to 50 times that of the intermediate of formula IV.

Ordinarily, the group R of the oxalate (formula III) decomposes in many cases, and the objective product (formula I) is obtained as free carboxylic acid. In the case where an ester is obtained depending on the conditions, it can be rendered into free carboxylic acid by ordinary hydrolysis for converting an ester into carboxylic acid. This is carried out, for example, by heating in a solvent such as water or aqueous dioxane for 5 to 20 hours at 25° to 130° C through the use of a base such as NaOH, KOH, $K_2CO_3$, or $Na_2CO_3$ or an acid such as hydrochloric acid, sulfuric acid, or hydrobromic acid.

The free carboxylic acid of formula I thus obtained can be rendered into a pharmaceutically acceptable salt by causing it to react with a metal or an amine cation. Example of the metal are Na, K, Mg, Ca, Al, and Cu. Examples of the amine cation are ammonia, tris (hydroxymethyl) aminomethane, N, N-bis (hydroxyethyl) piperazine, 2-amino-2-methyl-1-propanol, and 2,2-bis(-hydroxymethyl)-2,2',2''-nitrilotriethanol.

QUINOLOPYRAN-4-ONE-2-CARBOXYLIC ACID DERIVATIVE OF FORMULA I

Specific examples of compounds represented by formula I of this invention are set forth in the following table. It should be understood, of course, that these examples are set forth as illustrative only and are not intended to limit the scope of the invention.

tiveness of these medicines may be attributed to their suppression of release of a chemical mediator from mast cells as a result of antigen antibody reaction arising from reaginic antibodies.

The 50% lethal dose ($LD_{50}$) of a compound of this invention is i.v. 150 to 560 mg/kg. of a mouse, and the 50% effective dose ($ED_{50}$) is 0.5 mg. or less. Accordingly, the safety margin ($LD_{50}/ED_{50}$) is more than

| Compound No. | Compound | Melting Point (° C) | Mass | IR (KBr) (cm$^{-1}$) | NMR |
|---|---|---|---|---|---|
| 1 | 7,8-dimethyl-5-hydroxy-quinolo[4,3-b]-pyran-4-one-2-carboxylic acid | 248 – 250 | 285 ($M^{M+}$) | 3200,1710–1680,1620 | (($CH_2OH)_3C—NH_2$ Salt $D_2O$) 7.0–6.5 ppm, 2H(m), 6.3ppm, 1H(S), 1.9ppm, 3H(S), 1.65ppm, 3H(S) |
| 2 | 9-methyl-5-hydroxy-quinolo [4,3-b]-pyran-4-one-2-carboxylic acid | 245 – 249 | 271 ($M^+$) | 3500,1720–1690,1605 | — |
| 3 | 7-methyl-5-hydroxy-quinolo [4,3-b]-pyran-4-one-2-carboxylic acid | 243 – 244 | 271 ($M^+$) | 3200,1710–1670,1620 | — |
| 4 | 9-methoxy-5-hydroxy-quinolo[4,3-b]-pyran-4-one-2-carboxylic acid | 235 – 238 | 243 ($M^+$−44) | 3400,1690 | (Heavy DMSO) 7.3–7.1/ppm 3H(m) 5.9ppm/ H(S) |
| 5 | 7-methoxy-5-hydroxy-quinolo[4,3-b]-pyran-4-one-2-carboxylic acid | 245 – 247 | 243 ($M^+$−44) | 3150,1700–1680,1620 | — |
| 6 | 9-n-butyl-5-hydroxy-quinolo[4,3-b]-pyran-4-one-2-carboxylic acid | 218 – 220 (decomposes) | 313($M^+$) | 3400,1700 | — |
| 7 | 9-chloro-5-hydroxy-quinolo[4,3-b]-pyran-4-one-2-carboxylic acid | 225 – 240 | 291($M^+$) | — | — |
| 8 | 9-benzyloxy-5-hydroxy-quinolo[4,3-b]-pyran-4-one-2-carboxylic acid | 300(min.) | 363($M^+$) | 3400,3100–2800,1700 | — |
| 9 | 9-ethoxycarbonyl-5-hydroxy-quinolo[4,3-b]-pyran-4-one-2-carboxylic acid | 252 – 253 | 285 ($M^+$−44) | 3400,1720 1680,1620 | — |
| 10 | 9-phenyl-5-hydroxy-quinolo[4,3-b]-pyran-4-one-2-carboxylic acid | 239 – 248 (decomposes) | 285 ($M^+$−44) | 3400,3020 1710–1660 1640 | — |
| 11 | 7-methyl-8-chloro-5-hydroxy-quinolo[4,3-b]-pyran-4-one-2-carboxylic acid | 300(min.) | 305($M^+$) | 3400,3200–2900,1700, 1600 | — |
| 12 | 7,9-dimethyl-5-hydroxy-quinolo[4,3-b]-pyran-4-one-2-carboxylic acid | 249 – 252 | 285($M^+$) | 3200,1710–1670,1620 | — |
| 13 | 9-bromo-5-hydroxy-quinolo[4,3-b]-pyran-4-one-2-carboxylic acid | 300(min.) | 335($M^+$) | 3400,1690 | — |
| 14 | 9-fluoro-5-hydroxy-quinolo[4,3-b]-pyran-4-one-2-carboxylic acid | 258 – 259 | 275(M ) | 3100–2800, 1710—1660 | — |
| 15 | 8-methoxy-5-hydroxy-quinolo[4,3-b]-pyran-4-one-2-carboxylic acid | 245 – 249 | 243 ($M^+$−44) | 3400,1700, 1630 | — |
| 16 | 8,9-dimethoxy-5-hydroxy-quinolo[4,3-b]-pyran-4-one-2-carboxylic acid | 215 – 217 (decomposes) | 317($M^+$) | 3400,1700–1660 | — |
| 17 | 9-ethyl-5-hydroxy-quinolo[4,3-b]-pyran-4-one-2-carboxylic acid | 234 (decomposes) | 285($M^+$) | 3400,3100–2800, 1680 | — |
| 18 | tris (hydroxymethyl) methylammonium salt of 7,8-dimethyl-5-hydroxy-quinolo[4,3-b]-pyran-4-one-2-carboxylic acid | 201 – 202 | — | — | — |
| 19 | sodium salt of 9-methoxy-5-hydroxy-quinolo[4,3-b]-pyran-4-one-2-carboxylic acid | 300 (min.) | — | — | — |
| 20 | sodium salt of 7,8-dimethyl-5-hydroxy-quinolo[4,3-b]-pyran-4-one-2-carboxylic acid | 300 (min.) | — | — | — |

In view of activity on treatment of allergic asthma, the compounds may be classified into three, the first group being the most preferable, the second group being more preferable, the third group being preferable; compounds 1, 2, 7 and and their pharmaceutically acceptable salts, such as sodium salt and tris (hydroxymethyl)-methyl ammonium salt; compounds 3 through 6, 8, 9, 11 and their pharmaceutically acceptable salts, such as sodium salt and tris (hydroxymethyl)-methyl ammonium salt; and compounds 10, 12 through 17 and their pharmaceutically acceptable salts, such as sodium salt and tris (hydroxymethyl)-methyl ammonium salt.

TREATMENT OF ALLERGIC ASTHMA

The compounds of this invention are useful as new medicines for treatment of allergic asthma. The effec- 1,000, whereby the safety of the compound as a medicine is high. Particularly in the case of 7,8-dimethyl-5-hydroxy-quinolo [4,3-b]-pyran-4-one-2-carboxylic acid, the $LD_{50}$ is i.v. 560 mg./kg. of a mouse, and the $ED_{50}$ is less than 0.03 mg.. Therefore, the safety margin becomes 20,000, which is very high.

These medicines may be effectively administered in the following manner in the stated dosages. In the case of inhalation, a dose of 1 to 20 mg. is inhaled into the bronchus 3 to 4 times daily. In the case of intravenation, a dose of 1 to 10 mg. is injected 4 to 5 times daily. In the case of oral administration, a dose of 10 to 100 mg. is administered 3 times daily.

An antiallergic medicine of this invention for treatment of asthma is a compound of the general formula I or a salt thereof. Accordingly, a medicine of this invention can be one member or a mixture of two or more members selected from the group consisting of compounds of formula I and salts thereof and can be used as a composition containing a carrier for manufacture of medicines, a diluent, and other additives of ordinary kind.

Example of Test

To test the effectiveness of compounds of this invention for treatment of allergic asthma, evaluation of antiallergy effect was carried out by passive cutaneous anaphylaxis tests (PCA) on rats.

Rats (SLC-strain Wistar rat) were immunized with egg albumin which had been recrystallized five times and Bodetella pertussis vaccine, and, after 13 days, serum was taken from these rats. The serum thus obtained contained an antibody having characteristics similar to those of human reaginic antibody and exhibited an antibody titre of 256 or more.

This serum was diluted to 1/128 and intradermally injected into the back of rats. 48 hours thereafter, the compounds of the invention as set forth in the following table in the form of salts thereof with tris (hydroxymethyl) methyl ammonium dissolved in saline in the indicated quantities as the salts were administered intravenously, and 5 minutes thereafter, saline in which egg albumin and Evans Blue were dissolved was challenged intravenously. After 30 minutes, the animals were killed and the skins were removed and the quantity of the Evans Blue which has leaked as a result of the antigen antibody reaction was extracted through the use of $Na_2SO_4$ solution and acetone, colorimetry being carried out at 620 m$\mu$. The results are set forth in the following table.

In order to indicate still more fully the nature of this invention, the following specific examples of production of the compounds of the invention are set forth in concrete terms, it being understood in this case also that these production examples are presented as illustrative only and are not intended to restrict the scope of the invention.

Production Example 1

Production of 7,8-dimethyl-5-hydroxy-quinolo [4,3-b]-pyran-4-one-2-carboxylic acid (Compound 1)

Sodium ethylate was prepared from 450 mg. of sodium and 4.5 ml. of anhydrous ethanol, and 7.5 ml. of anhydrous benzene was added to this sodium ethylate. To the resulting suspension, 2.2 ml. of diethyl oxalate and 693 mg. of 7,8-diethyl-2,4-dihydroxy-3-acetyl-quinoline were added, and the resulting batch was agitated under reflux for 2 hours. The batch was then concentrated, and water was added thereto. The pH value of the resulting solution was adjusted at 4 to 5 with acetic acid, and the deposited crystals were filtered out and dried. A mixture of 6 ml. of glacial acetic acid and 2.2 ml. of concentrated hydrochloric acid was added to these crystal, and the resulting mixture was agitated under reflux for 40 minutes. The resulting batch was cooled and poured into chilled water, the crystals thereby depositing were filtered out and dried, whereupon 552 mg. (yield 65 percent) of crystals of a compound having the following formula and a melting point of 248° to 250° C was obtained.

| Compound No. | Compound | Dose mg*/kg | Inhibition rate % |
|---|---|---|---|
| 1 | 7,8-dimethyl-5-hydroxy-quinolo[4,3-b]-pyran-4-one-2-carboxylic acid | 3<br>0.3 | 100<br>98 |
| 2 | 9-methyl-5-hydroxy-quinolo[4,3-b]-pyran-4-one-2-carboxylic acid | 3<br>0.3 | 100<br>63 |
| 3 | 7-methyl-5-hydroxy-quinolo[4,3-b]-pyran-4-one-2-carboxylic acid | 3<br>0.3 | 100<br>27 |
| 4 | 9-methoxy-5-hydroxy-quinolo[4,3-b]-pyran-4-one-2-carboxylic acid | 3<br>0.3 | 98<br>38 |
| 5 | 7-methoxy-5-hydroxy-quinolo[4,3-b]-pyran-4-one-2-carboxylic acid | 3<br>0.3 | 98<br>37 |
| 6 | 9-n-butyl-5-hydroxy-quinolo[4,3-b]-pyran-4-one-2-carboxylic acid | 3<br>0.3 | 94<br>26 |
| 7 | 9-chloro-5-hydroxy-quinolo[4,3-b]-pyran-4-one-2-carboxylic acid | 3<br>0.3 | 100<br>67 |
| 8 | 9-benzyloxy-5-hydroxy-quinolo[4,3-b]-pyran-4-one-2-carboxylic acid | 3<br>0.3 | 96<br>34 |
| 9 | 9-ethoxycarbonyl-5-hydroxy-quinolo[4,3-b]-pyran-4-one-2-carboxylic acid | 3<br>0.3 | 100<br>39 |
| 10 | 9-phenyl-5-hydroxy-quinolo[4,3-b]-pyran-4-one-2-carboxylic acid | 3 | 90 |
| 11 | 7-methyl-8-chloro-5-hydroxy-quinolo[4,3-b]-pyran-4-one-2-carboxylic acid | 3<br>0.3 | 87<br>26 |
| 12 | 7,9-dimethyl-5-hydroxy-quinolo[4,3-b]-pyran-4-one-2-carboxylic acid | 3 | 90 |
| 13 | 9-bromo-5-hydroxy-quinolo [4,3-b]-pyran-4-one-2-carboxylic acid | 3 | 90 |
| 14 | 9-fluoro-5-hydroxy-quinolo [4,3-b]-pyran-4-one-2-carboxylic acid | 3 | 90 |
| 15 | 8-methoxy-5-hydroxy-quinolo [4,3-b]-pyran-4-one-2-carboxylic acid | 3 | 90 |
| 16 | 8,9-dimethoxy-5-hydroxy-quinolo [4,3-b]-pyran-4-one-2-carboxylic acid | 3 | 90 |
| 17 | 9-ethyl-5-hydroxy-quinol. [4,3-b]-pyran-4-one-2-carboxylic acid | 3 | 90 |

*The quantity as the tris (hydroxymethyl) methyl ammonium salt.

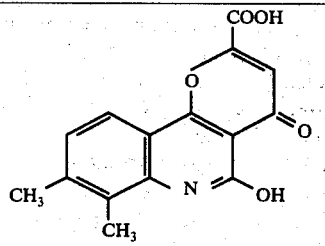

Elementary analysis value: $C_{15}H_{11}O_5N$

|  | C | H | N |
|---|---|---|---|
| Calculated | 63.16 % | 3.89 % | 4.91 % |
| Measured | 62.84 % | 4.11 % | 4.59 % |

Mass: 285 (M⁺)
IR(KBr): 3200 cm$^{-1}$, 1710-1680 cm$^{-1}$, 1620 cm$^{-1}$
NMR [$(CH_2OH)_3C—NH_2$salt, $D_2O$] 7.0 – 6.5 ppm.2HZ(m).
6.3 ppm./H(S)
1.9 ppm. 3H(S)
1.65 ppm.3H(S)

In the same manner as described above, Compounds 2 through 17 are produced from 2,4-dihydroxy-3-acetyl-quinoline having appropriate substituents.

Production Example 2

Production of tris (hydroxymethyl) methylammonium salt of 7,8-dimethyl-5-hydroxy-quinolo [4,3-b]-pyran-4-one-2-carboxylic acid (Compound 18)

285 mg. of 7,8-dimethyl-5-hydroxy-quinolo [4,3-b]-pyran-4-one-carboxylic acid and 242 mg. of tris (hydroxymethyl) aminomethane were dissolved in 2 ml. of water, and the resulting solution was decolored by treatment with activated carbon. Ethanol was added to this solution thereby to cause depositing of crystals, whereupon 260 mg. of a white powder of a melting point of 201° to 202° C was obtained.

Similar, tris (hydroxymethyl) methylammonium salts are produced with respect to Compounds 2 through 17.

Production Example 3

Production of a sodium salt of 9-methoxy-5-hydroxy-quinolo [4,3-b]-pyran-4-one-2-carboxylic acid (Compound 19)

1.15 g. of 9-methoxy-5-hydroxy-quinolo [4,3-b]-pyran-4-one-2-carboxylic acid and 212 mg. of sodium carbonate were added to 25 ml. of water, and the resulting batch was heated and agitated for 1 hour. Thereafter, 10 ml. of concentrated ethanol was added to the batch, and the solid precipitating out was filtered out, whereupon 1.16 g. of a white powder of a melting point above 300° C was obtained.

Similarly, sodium salts also with respect to Compounds 1, 2, and 3 and 5 through 17 are obtained.

We claim:

1. A quinolopyran-4-one-2-carboxylic acid of the formula

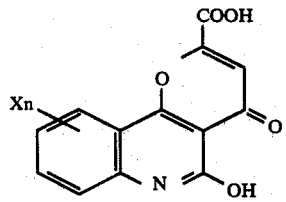

wherein X designates a member selected from the group consisting of non-tertiary alkyl groups having 1 to 5 carbon atoms, alkoxy groups having 1 to 5 carbon atoms, a halogen atom, aryl-substituted alkoxy groups having 7 to 10 total carbon atoms wherein aryl is phenyl, tolyl or xylyl, alkoxycarbonyl groups having 2 to 6 total carbon atoms, phenyl, tolyl and xylyl and n is 1 or 2 thereof.

2. The compound as claimed in claim 1 in which said quinolopyran-4-one-2-carboxylic acid is 7,8-dimethyl-5-hydroxy-quinolo [4,3-b]-pyran-4-one-2-carboxylic acid.

3. The compound as claimed in claim 1 in which said quinolopyran-4-one-2-carboxylic acid is 9-methyl-5-hydroxy-quinolo [4,3-b]-pyran-4-one-2-carboxylic acid.

4. The compound as claimed in claim 1 in which said quinolopyran-4-one-2-carboxylic acid is 7-methyl-5-hydroxy-quinolo [4,3-b]-pyran-4-one-2-carboxylic acid.

5. The compound as claimed in claim 1 in which said quinolopyran-4-one-2-carboxylic acid is 9-methoxy-5-hydroxy-quinolo [4,3-b]-pyran-4-one-2-carboxylic acid.

6. The compound as claimed in claim 1 in which said quinolopyran-4-one-2-carboxylic acid is 7-methoxy-5-hydroxy-quinolo [4,3-b]-pyran-4-one-2-carboxylic acid.

7. The compound as claimed in claim 1 in which said quinolopyran-4-one-2-carboxylic acid is 9-n-butyl-5-hydroxy-quinolo [4,3-b]-pyran-4-one-2-carboxylic acid.

8. The compound as claimed in claim 1 in which said quinolopyran-4-one-2-carboxylic acid is 9-chloro-5-hydroxy-quinolo [4,3-b]-pyran-4-one-2-carboxylic acid.

9. The compound as claimed in claim 1 in which said quinolopyran-4-one-2-carboxylic acid is 9-benzyloxy-5-hydroxy-quinolo [4,3-b]-pyran-4-one-2-carboxylic acid.

10. The compound as claimed in claim 1 in which said quinolopyran-4-one-2-carboxylic acid is 9-ethoxycarbonyl-5-hydroxy-quinolo [4,3-b]-pyran-4-one-2-carboxylic acid.

11. The compound as claimed in claim 1 in which said quinolopyran-4-one-2-carboxylic acid is 9phenyl-5-hydroxy-quinolo [4,3-b]-pyran-4-one-2-carboxylic acid.

12. The compound as claimed in claim 1 in which said quinolopyran-4-one-2-carboxylic acid is 7-methyl-8-chloro-5-hydroxy-quinolo [4,3-b]-pyran-4-one-2-carboxylic acid.

13. The compound as claimed in claim 1 in which said quinolopyran-4-one-2-carboxylic acid is 7,9-dimethyl-5-hydroxy-quinolo [4,3-b]-pyran-4-one-2-carboxylic acid.

14. The compound as claimed in claim 1 in which said quinolopyran-4-one-2-carboxylic acid is 9-bromo-5-hydroxy-quinolo [4,3-b]-pyran-4-one-2-carboxylic acid.

15. The compound as claimed in claim 1 in which said quinolopyran-4-one-2-carboxylic acid is 9-fluoro-5-hydroxy-quinolo [4,3-b]-pyran-4-one-2-carboxylic acid.

16. The compound as claimed in claim 1 in which said quinolopyran-4-one-2-carboxylic acid is 8-methoxy-5-hydroxy-quinolo [4,3-b]-pyran-4-one-2-carboxylic acid.

17. The compound as claimed in claim 1 in which said quinolopyran-4-one-2-carboxylic acid is 8,9-dimethoxy-5-hydroxy-quinolo [4,3-b]-pyran-4-one-2-carboxylic acid.

18. The compound as claimed in claim 1 in which said quinolopyran-4-one-2-carboxylic acid is 9-ethyl-5-hydroxy-quinolo [4,3-b]-pyran-4-one-2-carboxylic acid.

19. The compound as claimed in claim 1 in which said quinolopyran-4-one-2-carboxylic acid is tris (hydroxymethyl) methylammonium salt of 7,8-dimethyl-5-hydroxy-quinolo [4,3-b]-pyran-4-one-2-carboxylic acid.

20. The compound as claimed in claim 1 in which said quinolopyran-4-one-2-carboxylic acid is sodium salt of 9-methoxy-5-hydroxy-quinolo [4,3-b]-pyran-4-one-2-carboxylic acid.

21. The compound of claim 1 wherein X is phenyl.

22. The compound of claim 1 wherein X is a phenyl-substituted alkoxy group having 7 to 10 total carbon atoms.

23. A medicinal composition for treatment of allergic asthma comprising an amount effective for treatment of allergic asthma of a member selected from the group consisting of quinolopyran-4-one-2-carboxylic acids of the formula

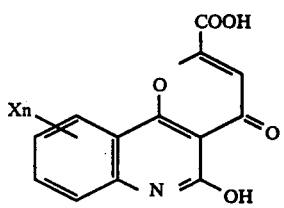

wherein X designates a member selected from the group consisting of non-tertiary alkyl groups having 1 to 5 carbon atoms, alkoxy groups having 1 to 5 carbon atoms, a halogen atom, aryl-substituted alkoxy groups having 7 to 10 total carbon atoms, alkoxycarbonyl groups having 2 to 6 total carbon atoms, and aryl groups having 6 to 10 carbon atoms, and $n$ is 1 or 2, X being the same group or different groups in the case where $n$ is 2, and salts of said derivatives; and a pharmaceutically acceptable carrier.

24. The medicinal composition for treatment of allergic asthma as claimed in claim 23 in which said member is selected from 7,8-dimethyl-5-hydroxy-quinolo [4,3-b]-pyran-4-one-2-carboxylic acid and pharmaceutically acceptable salts thereof.

25. The medicinal composition for treatment of allergic asthma as claimed in claim 23 in which said member is selected from 9-methyl-5-hydroxy-quinolo [4,3-b]-pyran-4-one-2-carboxylic acid and pharmaceutically acceptable salts thereof.

26. The medicinal composition for treatment of allergic asthma as claimed in claim 23 in which said member is selected from 7-methyl-5-hydroxy-quinolo [4,3-b]-pyran-4-one-2-carboxylic acid and pharmaceutically acceptable salts thereof.

27. The medicinal composition for treatment of allergic asthma as claimed in claim 23 in which said member is selected from 9-methoxy-5-hydroxy-quinolo [4,3-b]-pyran-4-one-2-carboxylic acid and pharmaceutically acceptable salts thereof.

28. The medicinal composition for treatment of allergic asthma as claimed in claim 23 in which said member is selected from 7-methoxy-5-hydroxy-quinolo [4,3-b]-pyran-4-one-2-carboxylic acid and pharmaceutically acceptable salts thereof.

29. The medicinal composition for treatment of allergic asthma as claimed in claim 23 in which said member is selected from 9-n-butyl-5-hydroxy-quinolo [4,3-b]-pyran-4-one-2-carboxylic acid and pharmaceutically acceptable salts thereof.

30. The medicinal composition for treatment of allergic asthma as claimed in claim 23 in which said member is selected from 9-chloro-5-hydroxy-quinolo [4,3-b]-pyran-4-one-2-carboxylic acid and pharmaceutically acceptable salts thereof.

31. The medicinal composition for treatment of allergic asthma as claimed in claim 23 in which said member is selected from 9-benzyloxy-5-hydroxy-quinolo [4,3-b]-pyran-4-one-2-carboxylic acid and pharmaceutically acceptable salts thereof.

32. The medicinal composition for treatment of allergic asthma as claimed in claim 23 in which said member is selected from 9-ethoxycarbonyl-5-hydroxy-quinolo [4,3-b]-pyran-4-one-2-carboxylic acid and pharmaceutically acceptable salts thereof.

33. The medicinal composition for treatment of allergic asthma as claimed in claim 23 in which said member is selected from 9-phenyl-5-hydroxy-quinolo [4,3-b]-pyran-4-one-2-carboxylic acid and pharmaceutically acceptable salts thereof.

34. The medicinal composition for treatment of allergic asthma as claimed in claim 23 in which said member is selected from 7-methyl-8-chloro-5-hydroxy-quinolo [4,3-b]-pyran-4-one-2-carboxylic acid and pharmaceutically acceptable salts thereof.

35. The medicinal composition for treatment of allergic asthma as claimed in claim 23 in which said member is selected from 7,9-dimethyl-5-hydroxy-quinolo [4,3-b]-pyran-4-one-2-carboxylic acid and pharmaceutically acceptable salts thereof.

36. The medicinal composition for treatment of allergic asthma as claimed in claim 23 in which said member is selected from 9-bromo-5-hydroxy-quinolo [4,3-b]-pyran-4-one-2-carboxylic acid and pharmaceutically acceptable salts thereof.

37. The medicinal composition for treatment of allergic asthma as claimed in claim 23 in which said member is selected from 9-fluoro-5-hydroxy-quinolo [4,3-b]-pyran-4-one-2-carboxylic acid and pharmaceutically acceptable salts thereof.

38. The medicinal composition for treatment of allergic asthma as claimed in claim 23 in which said member is selected from 8-methoxy-5-hydroxy-quinolo [4,3-b]-pyran-4-one-2-carboxylic acid and pharmaceutically acceptable salts thereof.

39. The medicinal composition for treatment of allergic asthma as claimed in claim 23 in which said member is selected from 8,9-dimethoxy-5-hydroxy-quino [4,3-b]-pyran-4-one-2-carboxylic acid and pharmaceutically acceptable salts thereof.

40. The medicinal composition for treatment of allergic asthma as claimed in claim 23 in which said member is selected from 9-ethyl-5-hydroxy-quinolo [4,3-b]-pyran-4-one-2-carboxylic acid and pharmaceutically acceptable salts thereof.

* * * * *